(12) United States Patent
Poulsen et al.

(10) Patent No.: US 6,340,357 B1
(45) Date of Patent: *Jan. 22, 2002

(54) DOSE SETTING DEVICE

(75) Inventors: Jens Ulrik Poulsen, Virum; Henrik Ljunggreen, Ballerup; Lars Hofmann Christensen, Frederiksberg, all of (DK)

(73) Assignee: Novo Nordisk A/S, Bagsvaerd (DK)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 09/360,263

(22) Filed: Jul. 26, 1999

Related U.S. Application Data

(62) Division of application No. 08/878,955, filed on Jun. 19, 1997, now Pat. No. 5,928,201.

(30) Foreign Application Priority Data

Jul. 5, 1996 (DK) ................................ 0750/96

(51) Int. Cl.⁷ ................................ A61M 5/00
(52) U.S. Cl. ........................ 604/208; 604/154
(58) Field of Search ................ 604/151, 152, 604/154, 207, 208, 232, 235, 67; 128/DIG. 1

(56) References Cited

U.S. PATENT DOCUMENTS

| | | | |
|---|---|---|---|
| 4,950,246 A | * 8/1990 | Muller | 604/154 |
| 5,139,484 A | * 8/1992 | Hazon et al. | 604/154 |
| 5,244,461 A | * 9/1993 | Derlien | 604/154 X |
| 5,425,716 A | 6/1995 | Kawasaki et al. | |
| 5,505,697 A | 4/1996 | McKinnon et al. | |
| 5,611,784 A | * 3/1997 | Barresi et al. | 128/DIG. 1 X |
| 5,681,285 A | 10/1997 | Ford et al. | |

FOREIGN PATENT DOCUMENTS

DE 3307810 9/1983

* cited by examiner

*Primary Examiner*—Anhtuan T. Nguyen
(74) *Attorney, Agent, or Firm*—Skadden, Arps, Slate, Meagher & Flom LLP

(57) ABSTRACT

The present invention relates to a drug delivery device wherein a dose to be apportioned from a cartridge is set by changing the relative position of co-operating dose setting elements (3, 5) and is injected by pressing a button (5) until this button abuts a stop (6). By operation of count up (7) or count down (8) buttons the dose is set and read into an electronic circuit (9) comprising a microprocessor and the dose setting movement of the dose setting elements relative to each other is performed by a motor (11) controlled by the circuit in accordance with the read in dose. The set dose is shown on a display (10). The motor (11) is further controlled to perform certain movements of the piston rod (3) so as retraction of this rod when a cartridge (1) is going to be changed an advancing of the piston rod to abutment with the piston (2) after the cartridge has been changed and further to advance this piston to expel air from the cartridge.

7 Claims, 1 Drawing Sheet

DOSE SETTING DEVICE

CROSS-REFERENCE TO APPLICATION

This application is a divisional of application Ser. No. 08/878,955 filed on Jun. 19, 1997, now U.S. Pat. No. 5,928,201 and claims priority under 35 U.S.C. 119 of Danish application serail no. 0750/96 filed Jul. 5, 1996, the contents of which are fully incorporated herein by reference.

STATEMENT REGARDING FEDERALLY SPONSORED RESEARCH OR DEVELOPMENT

Not applicable.

BACKGROUND OF THE INVENTION

The invention relates to drug delivery systems by which set doses may be apportioned from a cartridge and delivered, the dose setting being made by changing the relative position of cooperating dose setting elements and the delivery being made by pressing a button until it abuts a stop.

The deliverance may take place as an aerosol spray, an injection, or a high pressure jet which penetrates the skin so that the delivered material may be precipitated in the tissue beneath the skin.

The dose setting elements may be a threaded rod and a nut as in EP 327 910 wherein the threaded rod is a piston rod acting on a piston which presses out liquid from a cartridge in accordance with the distance the piston is moved. By dose setting a nut at the end of a hollow button surrounding a threaded piston rod is screwed along the piston rod away from a stop and thereby lifts the button up from the proximal end of the injection device. The injection is performed by pressing the button to move the nut back to the stop by which movement the piston rod and the piston is pressed into the cartridge a distance corresponding to the distance the nut was screwed away from the stop.

In another dose setting mechanism as described in WO 90/0038 a carrier, which may transport the piston rod in only a distal direction, is by the setting of a dose moved away from a stop and may thereafter by pressing an injection button be moved back to abutment with said stop.

In still another injection device as described in EP 0 245 312 a button with a push rod may be operated to reciprocate over a fixed distance. During part of its reciprocating movement the push rod drives a piston into a cartridge. Said part corresponds to a set dose which is set by varying a free space between the piston rod an the piston when the button and the push rod is in their not operated position.

The size of set doses is mainly indicated by a pointer or through a window which is coupled to one of the dose setting elements and indicates a number corresponding to the set dose on a scale coupled to the other dose setting element the size of the dose being proportional with the distance the two elements have been moved relative to each other. This fact sets a limit for the size of the figures on the scale although different initiatives has been taken to expand the space available for these figures. The dose setting is performed by turning a screw or a wheel or by rotating two parts of the injection device relative to each other and currently monitor the size of the dose set. By some constructions of the dose setting mechanism it is not possible to reduce the set dose if the two dose setting elements have been moved to far in relation to each other, i.e. if a too large dose has been set. By other constructions it is necessary to make sure that the device is reset before a dose can be set. A device which is very simple to use is aimed at. The simplest form of device should only show a very simple dose setting device and an injection button.

BRIEF SUMMARY OF THE INVENTION

It is the object of the invention to provide a user-friendly injection device by which more of the known draw-backs are avoided.

This is obtained by an injection device as described in the opening of this specification, which device is characterized in that the dose setting is read in into an electronic circuit and the dose setting movement of the dose setting elements relative to each other is performed by an electromechanical device, e.g. a motor, controlled by the electronic circuit in accordance with the read in dose setting.

According to the invention the electronic circuit may appropriately comprise a microprocessor.

The use of an electric motor in an injection device is known but in such known devices the motor is used to perform the injection. However, it has appeared that it is preferable to make the injection manually as this gives the user the possibility of adjusting the injection speed in accordance with the absorption of the injected liquid in the tissue. Further it is rather power consuming to perform the injection movement and consequently the batteries which must have small physical dimensions will be exhausted very quickly.

Combining electronic control and electromechanical setting of a dose enables the apparatus to intervene actively if anomalous or unintended conditions are detected during a dose setting sequence or if a not allowed handling of the apparatus is detected, so as opening of the cartridge holder during the setting of a dose. The active intervention may comprise a resetting of the dose setting to a starting point corresponding to the dose =0 and then a reporting of a malfunction until the error has been corrected, e.g. by closing the cartridge holder. This way the risk for erroneous doses and the doubts whether a correct dose is delivered or not may be overcome. When the error has been corrected or the unintended handling of the apparatus has stopped, the setting of the dose may be restarted from the starting position of the apparatus.

An electronically setting of the dose be performed by using one or two buttons by which a counting up or a counting down of a dose may be ordered to an electronic circuit.

The set dose may currently be shown on an electronic display and the counting may be performed upwards as well as downwards. The use of an electronic display offer the advantage that the size of the figures in the display depends only on the size of the display. Also other presentation devices than a display may be used, e.g. a speech synthesizer circuit currently pronouncing the number corresponding to the set dose.

The setting may be obtained by reading the wanted dose into the electronic circuit which present the read in dose in the display an controls the motor to run in a direction to set the mechanic parts of the dose setting mechanism accordingly. When a signal from a position reader indicates that the mechanic parts has reached a position corresponding to the set dose the electronic circuit will cause a stop of the motor.

The motor may be able to perform the mechanical setting at about the same speed as the counting up or down is performed on the display. If the mechanical setting is not obtained or is unbearably delayed in relation to the showing of the display it is taken as an indication of exhausted batteries and an error is reported to the user, e.g. by switching of the display.

Alternatively the reading of the display may be a feed back from a position reader reading the size of the mutual movement of the dose setting elements. In this way it is ensured that the dose setting is in accordance with the reading on the display as this reading is an expression of the actual relative position of the dose setting parts. In this embodiment an exhausted battery will result in a very slow or failing counting in the display.

In known motor driven delivery systems a set dose may be shown in a display and a count down may be shown concomitant with the motor driven injection. However, except from the showing of the display the set dose is not visually recognizable. In opposition thereto the electromechanical setting according to the invention will ensure that the setting further is physically recognizable as the physical position of the dose setting parts relative to each other may be visually inspected.

A switch may be provided which is operated when the injection button is pressed home. The operation of the switch ensures that the injection button is in its zero position before a new dose setting may be performed.

A further advantage by the device according to the invention is that limits may be set as an information read into the electronic circuit. If a maximum dose must not be exceeded the circuit may be so programmed that a number higher than the maximum number of units of the drug to be delivered cannot be read in into the electronic circuit.

Also the circuit may be programmed to set a predetermined dose every time the dose setting is operated. This may be of importance to people who are themselves unable to perform the setting.

The movement of the dose setting elements are recorded to the electronic circuit and is translated to a number indicating the set dose in units defined for the sort of medicine which is administered by the injection device. As medicine may occur with different concentrations and as from one type of medicine to another different volumes may corresponds to a unit, it is advantageous that the translation of movement into units is made electronically so that the same mechanical device may be made useable for different types and concentrations of medicine just by a programming of the circuit. The programming of the circuit may co-operate with a code on the cartridge so that the program is automatically adapted to the medicine in the cartridge and the correct amount is delivered when a dose is set by its number of units.

BRIEF DESCRIPTION OF THE DRAWINGS

In the following the invention is described with references to the drawing which schematically shows an electronic dose setting device according to the invention.

DETAILED DESCRIPTION OF THE INVENTION

Figure 1:
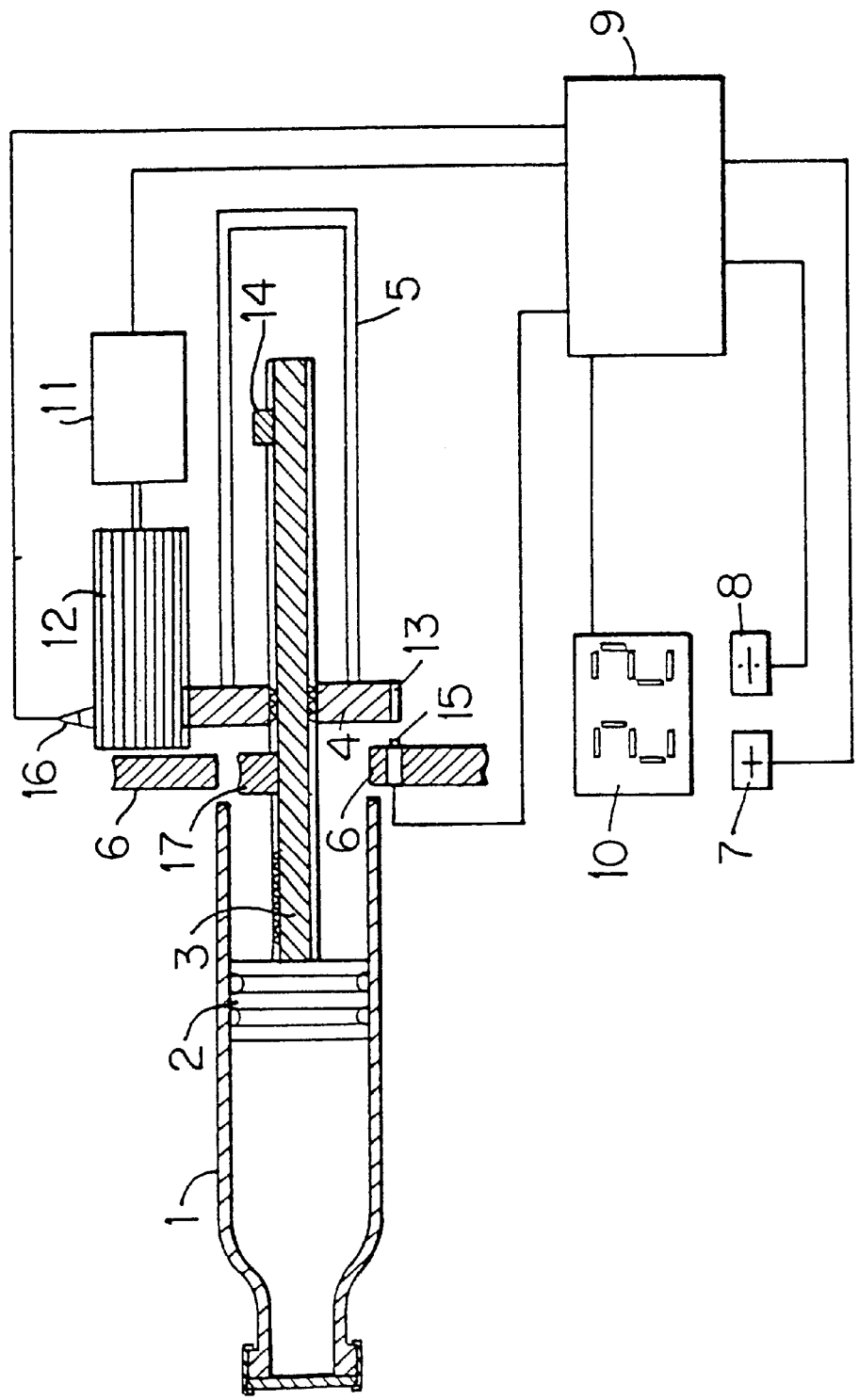

A cartridge 1 is accommodated in a not shown housing. By the use of the device a piston 2 is pressed into the cartridge 1 to press out some of the content of this cartridge through a not shown needle which may be mounted at a distal end of the cartridge. The piston is moved by a piston rod 3 which is shown as a threaded rod and forms a first dose setting element. A second dose setting element is a nut 4 with an internal thread co-operating with the external thread of the piston rod 3. A button with a bore accommodating an outer end of the piston rod 3 forms an integral part of the nut and forms an injection button 5. The injection button 5 may be pressed to move the piston 2 into the cartridge until the nut 4 abuts a stop 6 forming a part of the not shown housing. A pin 17 in the housing engages an axial track in the piston rod to block this piston rod against rotation relative to the housing.

When a dose is going to be set, the device is in an initial position with the nut 4 abutting the stop 6. The dose is set by activating one of a pair of dose setting buttons 7 and 8, one 7 for counting forward or up and another 8 for counting backward or down. The set dose is stored in an electronic circuit 9 and is displayed on a display 10. As long as the counting up button 7 is pressed the set dose is increased and the size of the dose may currently be followed on the display 10. If the counting up runs too far, the count down button 8 may be activated until the set dose is decreased to the size wanted.

The mechanical setting of the dose setting elements according to the electronically set dose is performed by an electric motor 11 having an output shaft provided with an elongated gear 12 which gear engages a toothing 13 at the periphery of the nut 4.

The motor 11 which may be controlled to run as well clockwise as anticlockwise is controlled from the electronic circuit to rotate the nut in accordance with the set dose. The rotation is measured by a position reader 16 which counts the number and direction of passing teeth.

To make sure that the electronically set dose is also mechanically set the display may be driven so that it does not show the setting until the feed-back signal from the position reader 16 confirms that the mechanical setting has taken place. Put in another way, when the count up button 7 is activated the circuit 9 controls the motor 11 to rotate in a dose increasing direction and the display will then currently show how far the nut is rotated in a direction corresponding to increasing settings. When the count down button 8 is activated a decrease of the mechanically set dose is obtained and recorded in the same way.

Alternatively a number is counted up in the display by activating the count up button 7, and the motor is then controlled to set the dose setting parts in a relative position corresponding to the number in the display. The motor and the battery must be powerful enough to ensure that the mechanical setting of the dose setting parts follows the counting up or down in the display very closely, i.e. with none or only a very small delay. When the delay exceeds a preset time, the electronic circuit may indicate an error, e.g. by switching off the display or by activating a "low battery" indicator.

If the count down button 8 is activated when the display shows zero which reading corresponds to the position of the nut 4 when it abuts the stop 6, it shall not be possible to set a negative dose. This may be avoided either by the fact that the nut 4 operates a switch 15 mounted in the stop 6 by which operation a signal is sent to the circuit 9 to stop further operation of the motor 11 in the dose decreasing direction. Alternatively the circuit 9 may currently monitor the power consumption of the motor 11 and stop this motor when a rise in power consumption indicates that the nut 4 is abutting the stop 6.

Correspondingly setting of a dose which exceed the amount of remaining medicine in the cartridge may be avoided by providing a stop 14 at the outer end of the piston rod the position of this stop being so that the cartridge is just empty when the nut 4 is screwed up to this stop and pressed to abutment with the stop 6. When the motor during setting of a dose is operated in the dose increasing direction to move the nut 4 towards the outer end of the piston rod suddenly increases its power consumption due to the fact that the nut 4 has reached the stop 14 on the piston rod 3 it is by the circuit taken as an indication of the fact that the set dose cannot be further increased and the motor will be stopped and the size of the set dose corresponding to the medicine remaining in the cartridge may be read out on the display 10.

By the motor driving of the mechanical setting the realization of the stops becomes very simple as the power of the motor is limited and the stops only have to influence the power consumption of the motor recognizably whereas manually operated devices may be exposed to heavy forces which the elements in the device shall be able to stand without breaking at the same time as the elements shall be miniaturized if the device shall not be inconveniently bulky. In fact the stops may be made pure electronically. It may be stored in the electronic circuit how many units of a drug the cartridge contains and the number of units delivered may be cumulated so that the circuit can calculate the number of units left in the cartridge and set this number as an upper limit for the dose which can be set.

The switch 15 in the stop may serve the function of indicating when the injection button is pressed home and an injection is completed. When the injection is pressed home it may further be locked in this position until a new dose is going to be set. When a signal indicating that an injection is completed is sent to the circuit 9 the size of the just completed injection is stored and may on demand be showed in the display until the next dose is set. This demand may be signalled in different ways, e.g. by a short pressing of one of the dose setting buttons, by a switch activated when a protection cap is removed from the housing, or by operating a button releasing the injection button from its pressed home position.

With the injection button in its pressed home position the motor can be used to automatically perform other functions to make the use of the device less complicated. When a cartridge has to be changed a cartridge holder shall be opened, the piston rod shall be moved back to a retracted position to clear a space for a new cartridge, the new cartridge shall be inserted, the cartridge holder shall be closed, and the piston rod shall be moved towards the piston to back-up this piston and then be moved further forwards to move the piston into the cartridge until air in this cartridge is pressed out through an injection needle. A switch detecting the opening of the cartridge holder sends a signal to the circuit to obtain operation of the motor in an dose decreasing direction. By this operation the nut may abut the stop 6 in a sliding way and draw the piston rod backward. When an increase in the motor power consumption indicates that the piston rod may not be drawn further backwards, the motor is stopped and the empty cartridge may be removed and replaced by a new full one. When the cartridge holder is closed the motor may be controlled to rotate in the opposite direction and if the nut is in some way blocked against movement along the piston rod, the piston rod will instead be moved into the cartridge and abut the piston. This abutment is indicated by a rise in the power consumption. The piston rod may move the piston further into the cartridge to drive out air from the cartridge on the condition that a needle is mounted and the device is held with the needle pointing up. When the air is pressed out of the cartridge a new rise in the power consumption indicates that the air is pressed out and now liquid is pressed out. This power consumption pattern may be stored in the circuit so the motor may be stopped when it is detected that liquid is beginning to be pressed out. Hereafter the device is ready for use. This ability to discriminate between the out pressing of air and liquid may be used for an automatic air shot function which may be activated before each use of the injection device.

What is claimed is:

1. A drug delivery device for dispensing set doses from a cartridge of the type containing medicine sufficient for a number of dosed injections and a piston which can be moved forward inside the cartridge to expel doses of medicine, said device comprising:

a cartridge holder having open and closed positions, and into which a cartridge can be loaded when in an open position;

a cartridge holder switch which generates a signal when said cartridge holder is moved from said open position to said closed position;

an electrical motor;

a piston rod coupled to said motor for movement responsive to activation of said motor; and an electronic circuit which receives said signal from said cartridge holder switch and activates said motor responsive to receiving said signal to move said piston rod in a first direction, towards the piston of a cartridge which has been loaded in said cartridge holder; and wherein said electronic circuit further includes a sensor to sense the power consumption of said motor and stops said motor, and thereby the movement of said piston rod in said first direction, upon detecting a predetermined increase in power consumption, indicating that the piston rod has encountered such a piston, whereby said circuit automatically sets a desired initial position of said piston rod whenever a new cartridge is loaded.

2. A drug delivery device as recited in claim 1, wherein said cartridge holder switch generates a cartridge holder open signal when said cartridge holder is opened and wherein, in response to said cartridge holder open signal, said electronic circuit activates said motor to move said piston rod in a direction opposite to said first direction, until reaching a predetermined retracted position.

3. A drug delivery device as recited in claim 2, wherein the predetermined retracted position is determined by sensing a predetermined increase in power consumption by the electrical motor.

4. A drug delivery device as recited in claim 3, wherein said electrical motor rotates a nut member having an inner thread mating an outer thread on said piston rod, such that said piston rod moves in a longitudinal direction when said nut member is locked against movement in said longitudinal direction and rotated.

5. A drum delivery device as recited in claim 4, further comprising a delivery button which is coupled to said nut member such that said delivery button moves a distance away from an original position when said nut member is rotated, which distance corresponds to the set dose.

6. A drug delivery device as recited in claim 5, further comprising a delivery button switch which is actuated when said button is pressed to its original position, wherein said delivery button switch is coupled to said electronic circuit such that said electronic circuit detects whether said delivery button is in said original position.

7. A drug delivery device as recited in claim 6, wherein said delivery button is releasably locked against movement when said delivery button is pressed to said original position.

* * * * *